(12) United States Patent
Pahan et al.

(10) Patent No.: US 11,844,767 B2
(45) Date of Patent: *Dec. 19, 2023

(54) COMPOSITION AND METHODS FOR STIMULATING CLEARANCE OF AMYLOID-BETA PROTEIN

(71) Applicant: Rush University Medical Center, Chicago, IL (US)

(72) Inventors: Kalipada Pahan, Skokie, IL (US); Arunava Ghosh, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 170 days.

This patent is subject to a terminal disclaimer.

(21) Appl. No.: 17/471,619

(22) Filed: Sep. 10, 2021

(65) Prior Publication Data

US 2021/0401772 A1 Dec. 30, 2021

Related U.S. Application Data

(63) Continuation of application No. 16/084,067, filed as application No. PCT/US2017/021799 on Mar. 10, 2017, now Pat. No. 11,135,180.

(60) Provisional application No. 62/308,374, filed on Mar. 15, 2016.

(51) Int. Cl.
| | | |
|---|---|---|
| A61K 31/07 | (2006.01) | |
| A61P 25/28 | (2006.01) | |
| A61K 31/192 | (2006.01) | |
| A61K 31/203 | (2006.01) | |
| A61K 9/00 | (2006.01) | |

(52) U.S. Cl.
CPC ............ *A61K 31/07* (2013.01); *A61K 31/192* (2013.01); *A61K 31/203* (2013.01); *A61P 25/28* (2018.01); *A61K 9/0019* (2013.01); *A61K 9/0053* (2013.01); *A61K 9/0085* (2013.01)

(58) Field of Classification Search
CPC ...... A61K 31/07; A61K 25/28; A61K 31/192; A61K 31/203; A61K 9/00
See application file for complete search history.

(56) References Cited

U.S. PATENT DOCUMENTS

2005/0031651 A1 2/2005 Garvais et al.
2017/0319531 A1 11/2017 Pahan

FOREIGN PATENT DOCUMENTS

WO 2016201086 A1 12/2016

OTHER PUBLICATIONS

Ashraf, et al., CNS Neurol Disord Drug Targets, 2014; 13(7): 1280-1293.
Moreno-Garcia Frontiers in Neuroscience (2018) vol. 12 article 464, 1-13.
Oakley, Holly, et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation", The Journal of Neuroscience, Oct. 4, 2006, 26(40):10129-10140, 12 pp.
Hachiya, Yasuo, et al., "Mechanisms of neurodegeneration in neuronal ceroid-lipfuscinoses", Acta Neuropathal, 2006, 111:168-177, DOI 10.1.007/s00401-005-0024-x, 10 pp.
Li, Meng, et al., "The role of intracellular amyloid β in Alzheimer's disease", Progress in Neurobiology, 2007 Elsevier Ltd., 83 131-139, 9 pp.
Baranello, Robert J., et al., "Amyloid-Beta Protein Clearance and Degradation (ABCD) Pathways and their Role in Alzheimer's Disease", HHS Public Access Author Manuscript, Published: Curr Alzheimer Res. 2015; 12(1): 32-46, 30 pp.
Takahashi, Reisuke H., et al., "Co-occurrence of Alzheimer's disease β-amyloid and tau pathologies at synapses", NIH Public Access Author Manuscript, Published: Neurobiol Aging, Jul. 2010; 31(7): 1145-1152. doi: 10.1016/j.neurobiolaging.2008.07.021, 15 pp.
Ghosh, A. et al.; "Gemfibrozil and Fenofibrate, Food and Drug Administration-approved Lipid-lowering Drugs, Up-regulate Tripeptidyl-peptidase 1 in Brain Cells via Peroxisome Proliferator-activated Receptor α"; The Journal of Biological Chemistry, vol. 287, No. 46; Sep. 2012; pp. 38922-38935.
Ghosh, A. et al.; "Activation of PPAR-a:RXRa pathway upregulates tripeptidyl peptidase 1 in brain cells: Implications for late infantile neuronal ceroid lipofuscinosis therapy"; Abstract; Molecular Genetics and Metabolism, vol. 108, No. 2; Feb. 2013; pp. S42-S43.
Ghosh, A. et al.; "PPARα in lysosomal biogenesis: A perspective"; Pharmacological Research, vol. 103; Nov. 2016; pp. 144-148.
Arlt, PD, MD, Sonke, et al., "Non-Alzheimer's disease-related memory impairment and dementia", Clinical research, AICH-Servier Research Group, 2013, 9 pp.
Eisenberg, David, et al., "The amyloid state of proteins in human diseases", Howard Hughes Medical Institute, Department of Biological Chemistry, UCLA, 2012, 30 pp.

*Primary Examiner* — Shirley V Gembeh
(74) *Attorney, Agent, or Firm* — Taft Stettinius & Hollister LLP; Joseph Bennett-Paris

(57) ABSTRACT

The present invention generally relates to compositions and methods for stimulating astroglial uptake and degradation of amyloid-β protein aggregates. One aspect of the invention provides a method of preventing or treating Alzheimer's disease including administrating a clinically effective amount of combination of vitamin A or a derivative thereof and an agonist of proliferator-activated receptor α ("PPARα") to a human or veterinary subject in need of such treatment.

16 Claims, 7 Drawing Sheets

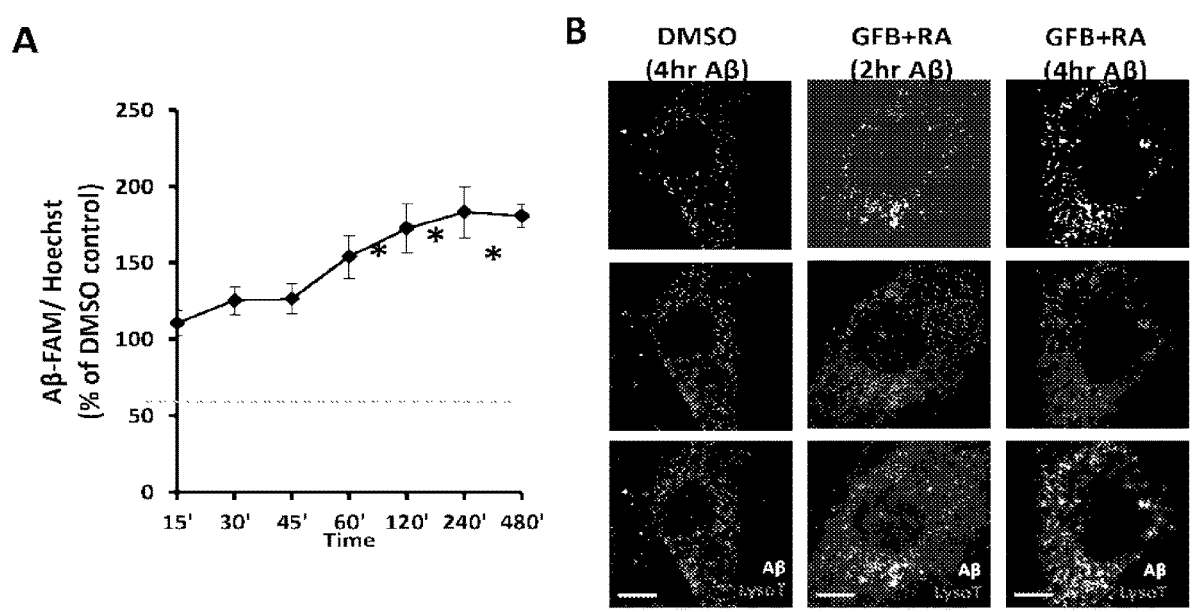
Figure 1(A-B)

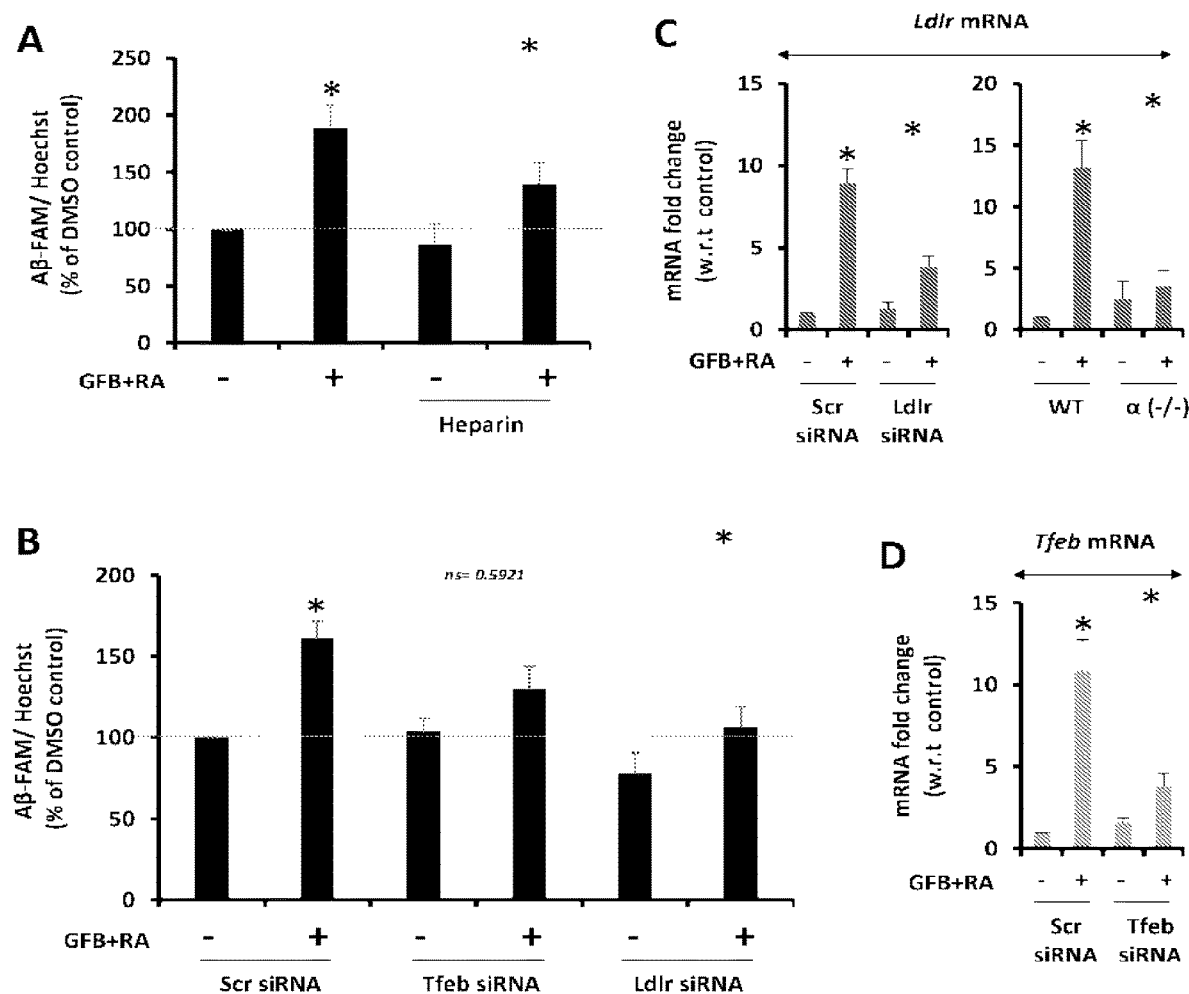
Figure 2(A-D)

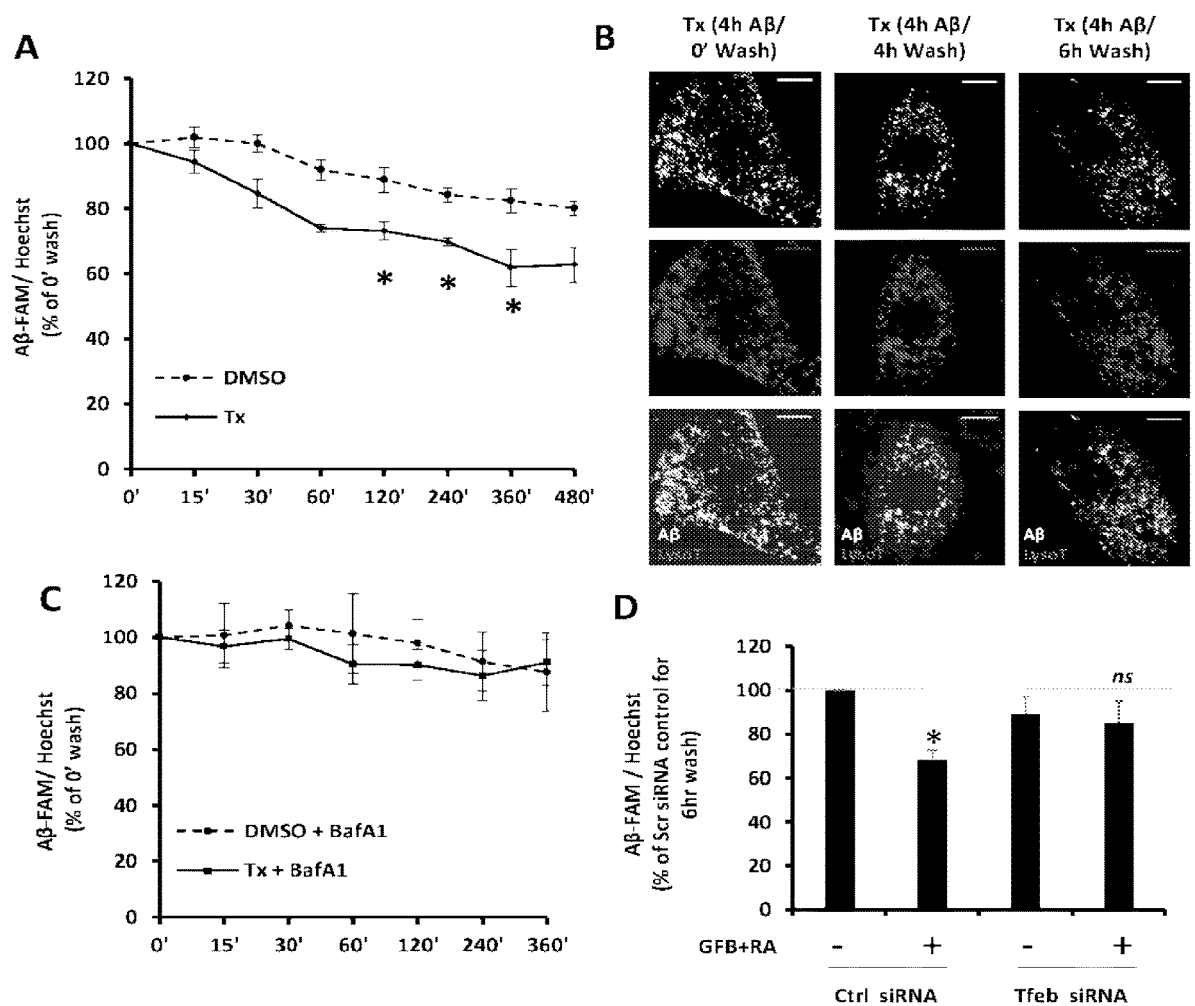
Figure 3(A-D)

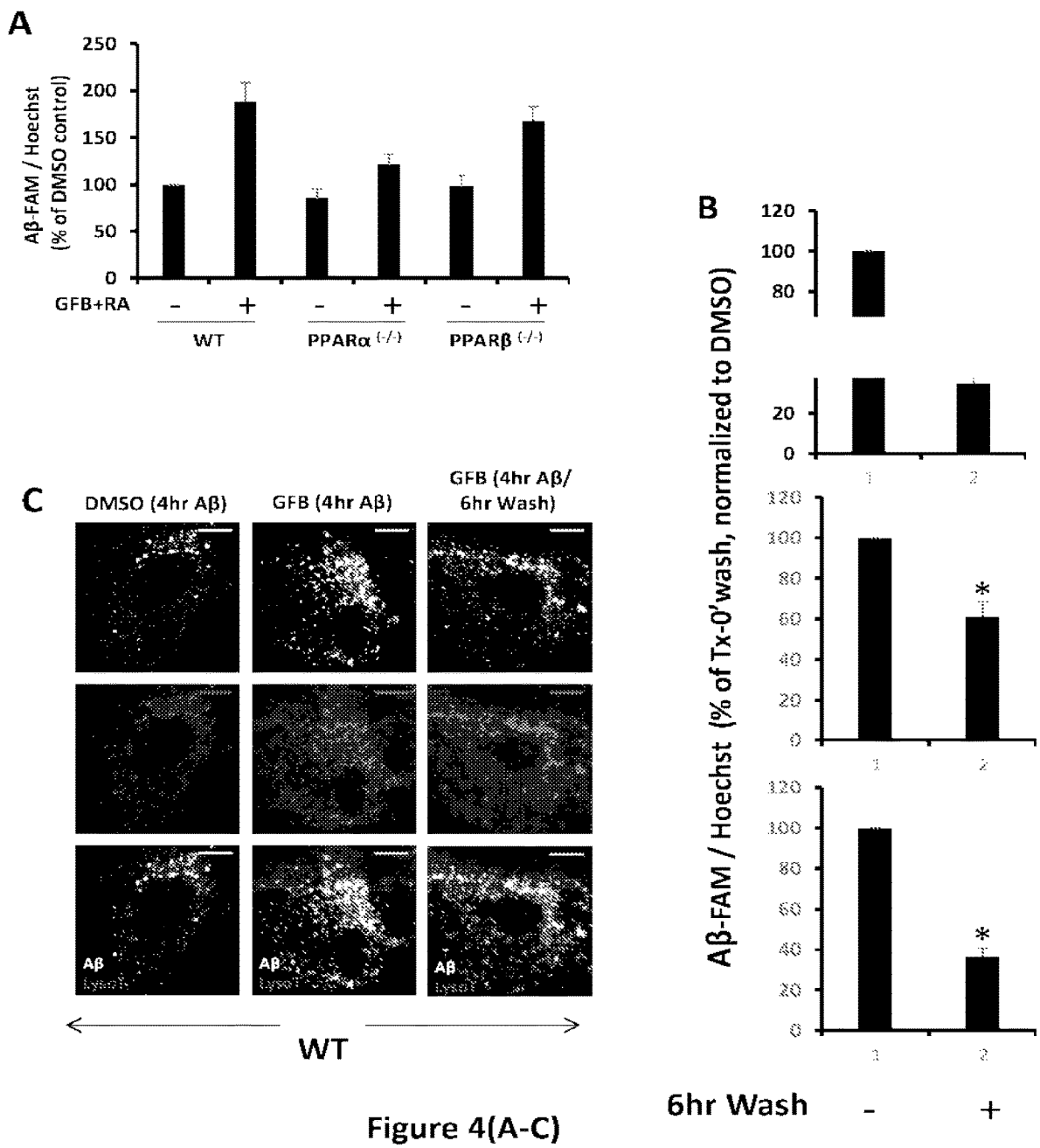
Figure 4(A-C)

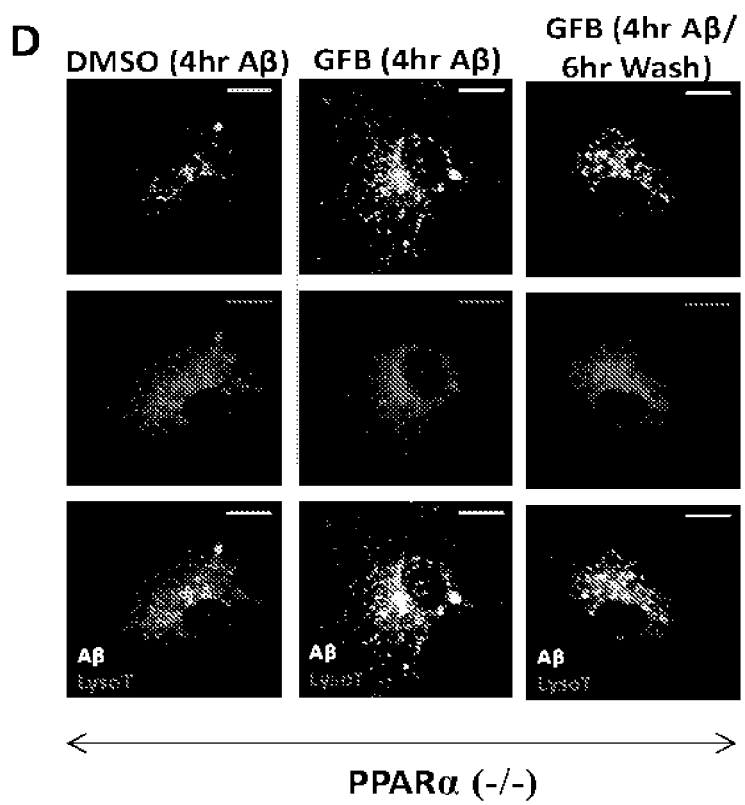
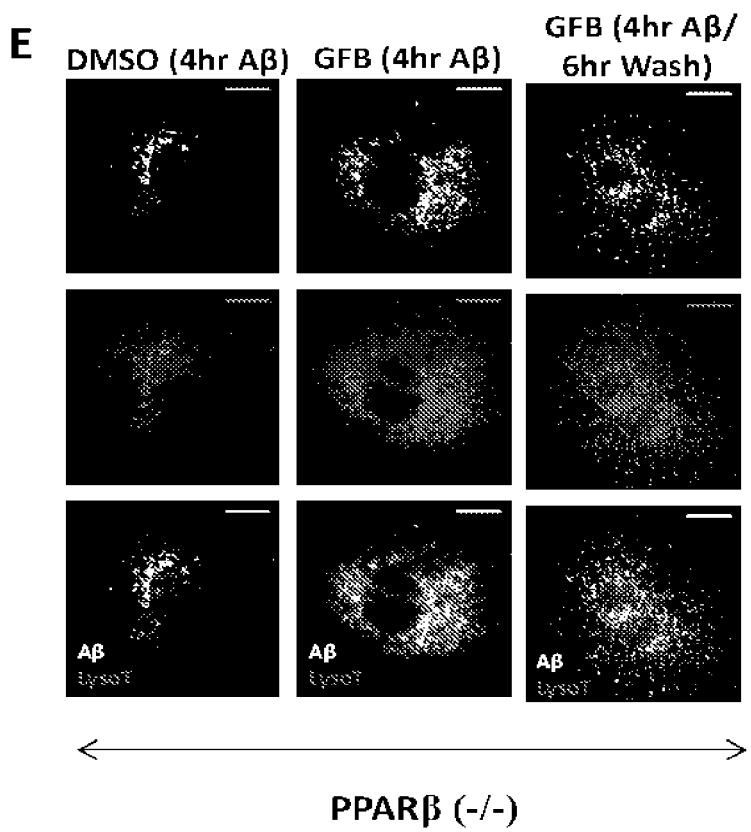
Figure 4(D-E)

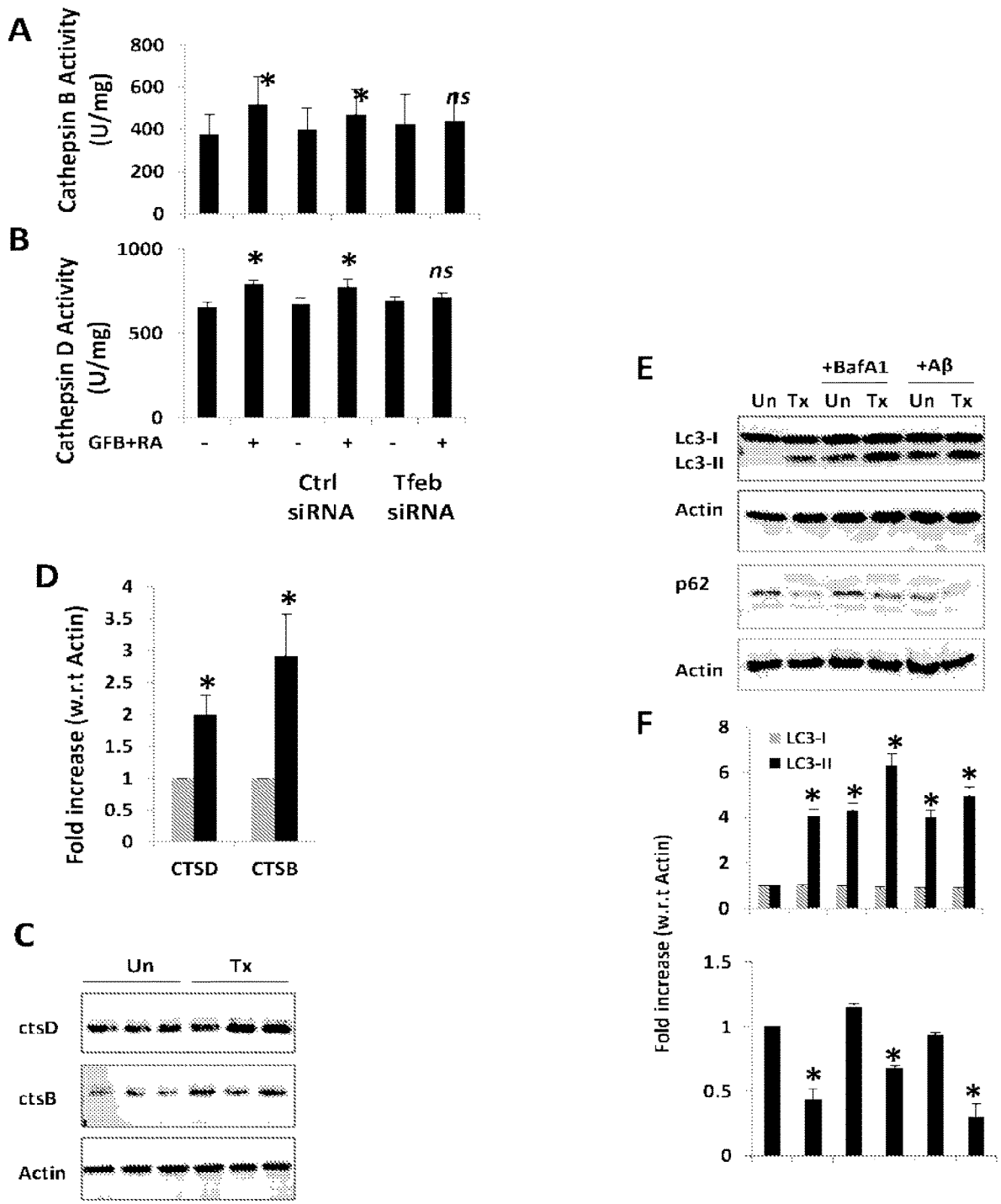
Figure 5(A-F)

COMPOSITION AND METHODS FOR STIMULATING CLEARANCE OF AMYLOID-BETA PROTEIN

CROSS-REFERENCE TO RELATED APPLICATIONS

This application is a continuation of application Ser. No. 16/084,067, filed Sep. 11, 2018, which is a national stage application of International Application No. PCT/US2017/021799 filed on Mar. 10, 2017, which claims the benefit of the filing date of U.S. Provisional Patent Application No. 62/308,374, filed Mar. 15, 2016, the contents of which is hereby incorporated by reference.

TECHNICAL FIELD

The present invention generally relates to compositions and methods for stimulating astroglial uptake and degradation of amyloid-3 protein aggregates. One aspect of the invention provides a method of preventing or treating Alzheimer's disease including administrating a clinically effective amount of combination of vitamin A or a derivative thereof and an agonist of proliferator-activated receptor α ("PPARα") to a human or veterinary subject in need of such treatment.

BACKGROUND

Alzheimer's disease is progressive neurodegenerative disease with classic memory impairment and cognitive disorder. The pathological hallmarks of Alzheimer's disease are presence of senile plaques (SPs), composed of oligomeric amyloid beta (Aβ40/42) and formation neurofibrillary tangles (NFTs), originating from Tau hyper-phosphorylation, in the cortex and hippocampus of brain (1,2). The abnormal accumulation of Aβ and formation NFTs induces neuro-inflammation and subsequent neuronal loss, which is the primary cause of Alzheimer's disease (3).

Aggregate prone A1340/42 fragments are generated by the sequential activity of β- and γ-secretase on amyloid precursor protein (APP), whereas the action of α-secretase produces soluble APP (sAPP) fragments that are not prone to aggregation (4,5). α-secretase is mainly associated to the plasma membrane, whereas majority of β-secretase is present in the endosomal-lysosomal compartments (6,7). Additionally, some of the cathepsins (D and E) could exhibit β-/γ-secretase like activity (8). The processing of APP could happen in either secretory pathway or endosomal-lysosomal pathway. Newly synthesized APP could be either be delivered to plasma membrane where it is processed mainly by α-secretase (secretory pathway), or occasionally the APPs are recycled back into endosomes by endocytosis, where it could be processed by β- and γ-secretase (endosomal-lysosomal pathway) producing Aβ fragments (9,10).

Under normal conditions, further cleavage by other proteases (mainly Cathepsin B) in the lysosomes degrade the Aβ fragments into even smaller non-toxic fragments, which are recycled or expunged from the cell (11). Also both in vitro and in vivo conditions, extracellular Aβ could also be endocytosed and degraded in the lysosomes (12). Decline in lysosomal function due to ageing or other pathological condition may result in abnormal accumulation of Aβ fragments inside the lysosome and increase the lysosomal load. This may lead to rupture of lysosomal membrane, which not only releases the toxic Aβ into the cytosol, but also trigger lysosomal membrane permeability (LMP) that can initiate necrotic or apoptotic cell death (13). Therefore, it is imperative that enhanced lysosomal function could be a possible therapeutic mechanism of Aβ clearance in Alzheimer's disease.

SUMMARY OF THE PREFERRED EMBODIMENTS

In one aspect, the present invention provides a method for reducing amyloid-β protein aggregates in the brain of a subject including administering to the subject in need of such treatment a composition including a therapeutically effective amount of a combination of an agonist of proliferator-activated receptor α ("PPARα") and vitamin A or a derivative thereof. In one embodiment, the agonist is an amphipathic carboxylic acid. In another embodiment the agonist is clofibrate, gemfibrozil, ciprofibrate, bezafibrate, clinofibrate or fenofibrate. The composition can also include at least one pharmaceutically acceptable carrier.

In another embodiment, the therapeutically effective amount is an amount that stimulates the uptake of amyloid-β protein by astrocytes present in the brain. In yet another embodiment, the therapeutically effective amount is an amount that stimulates degradation of amyloid-β protein by such astrocytes.

The subject may be a human subject, for example, a human subject exhibiting symptoms of Alzheimer's disease. The composition may be administered orally. Alternatively, the composition is administered by a subcutaneous, intra-articular, intradermal, intravenous, intraperitoneal or intramuscular route. In another embodiment, the composition is administered directly to the central nervous system.

Another expect of the invention provides a method for reducing amyloid-β protein aggregates in the brain of a subject's brain including administering a composition including a therapeutically effective amount of an agonist of proliferator-activated receptor α ("PPARα") to the subject. In certain embodiments the agonist is an amphipathic carboxylic acid. The agonist may be, for example, clofibrate, gemfibrozil, ciprofibrate, bezafibrate, clinofibrate or fenofibrate.

BRIEF DESCRIPTION OF THE DRAWINGS

FIGS. 1(A-B) illustrate that GFB and RA treatment enhances A13 uptake in mouse primary astrocytes: In FIG. 1(A), mouse primary astrocytes were treated for 24 hrs with GFB and RA, followed by incubation with 500 nM oligomeric FAM-tagged Aβ (1-42) for 15', 30', 45' 1 hr, 2 hr, 4 hr, 8 hr. Aβ uptake assay was performed as described herein. Data is represented a percentage change compared to DMSO treated control. FIG. 1(B) shows microscope photographs showing mouse primary astrocytes treated with GFB and RA and incubated with 500 nM HF-Aβ (1-42) and 75 nM Lysotracker Red before observation. S cale bar=20 μM. r<0.05 w.r.t DMSO treated control. All data are representative of the mean±SEM of three independent experiments.

FIGS. 2 (A-C) illustrate the effect of HSPG, TFEB and LDLR on GFB and RA mediated Aβ uptake in mouse primary astrocytes. FIG. 2(A): Mouse primary astrocytes were treated with DMSO or GFB-RA, followed by treatment with diluent of Heparin (100 μg/ml) and further incubated in 500 nM FAM-Aβ for 4 hrs. Aβ uptake assay was performed and data is represented as percentage change w.r.t untreated control. FIG. 2(B): Mouse primary astrocytes were transfected with scrambled siRNA, Tfeb siRNA or LDLR siRNA, treated with GFB-RA, followed by incubation in 500 nM FAM-Aβ for 4 hrs. Data from Aβ uptake assay is represented as percentage change w.r.t DMSO and scrambled siRNA treated control. FIG. 2(C) Quantitative RT-PCR was performed to measure the effectivity of LDLR silencing by siRNA and levels of LDLR in PPARα(−/−) cells. FIG. 2(D) Quantitative RT-PCR was performed to measure the effect of TFEB silencing by siRNA. p*<0.05 w.r.t control; ns-not significant. All data are representative of the mean±SEM of three independent experiments.

FIGS. 3(A-D) illustrate that GFB and RA treatment enhances Aβ degradation in mouse primary astrocytes: FIG. 3(A): Mouse primary astrocytes were treated for 24 hrs with GFB and RA, followed by incubation with 500 nM oligomeric FAM-tagged Aβ(1-42) for 4 hr and allowed to grow in Aβ-free media for 15′, 30′, 1 hr, 2 hr, 4 hr, 6 hr and 8 hr. Aβ degradation assay was performed as described in Methods section. Data was represented a percentage change compared to unwashed control. FIG. 3(B): Mouse primary astrocytes treated with GFB and RA were incubated with 500 nM HF-Aβ(1-42), washed for 4 h and 6 h, further incubated with 75 nM Lysotracker Red and observed under microscope. Scale bar=20 μM. p*<0.05 w.r.t unwashed control. FIG. 3(C): Mouse primary astrocytes were treated with GFB and RA for 24 hrs, followed by treatment with 100 nM Bafilomycin A1 for 45 mins, followed by incubation with 500 nM FAM-Aβ, washed in Aβ free media for 6 hrs and degradation assay was performed. Data is represented as percentage change w.r.t unwashed controls. FIG. 3(D): Aβ degradation assay was done in mouse primary astrocytes which were either transfected with scrambled siRNA or Tfeb siRNA, prior to treatment with DMSO or GFB-RA. Data is compared to DMSO treated, scrambled siRNA transfected controls. p*<0.05 w.r.t control; ns-not significant. All data are representative of the mean±SEM of three independent experiments. All data are representative of the mean±SEM of three independent experiments.

FIG. 4(A-E) illustrates the role of PPARα and PPARβ in Aβ uptake and degradation in mouse primary astrocytes. FIG. 4(A): Mouse primary astrocytes isolated from PPARα (−/−), PPARβ(−/−) and WT animals were isolated, treated with GFB-RA or DMSO, followed by incubation with 500 nM FAM-Aβ and subjected to Aβ uptake assay. Data was compared to DMSO-treated WT control and represented as percentage change. p*<0.05 w.r.t control; ns-not significant. FIG. 4(B): Mouse primary astrocytes isolated from PPARα (−/−), PPARβ(−/−) and WT animals were isolated, treated with GFB-RA, followed by incubation with 500 nM FAM-Aβ for 4 hrs, washed in Aβ free media for 6 hrs and subjected to Aβ degradation assay. Analysis of data is described in detail in Discussion. p*<0.05 w.r.t control; ns-not significant. Mouse primary astrocytes isolated from WT (FIG. 4(C)), PPARα(−/−)) FIG. 4(D)) and PPARβ(−/−) (FIG. 4(E)) animals were isolated, treated with DMSO, followed by incubation with 500 nM HF-647-Aβ for 4 hrs and 75 nM Lysotracker for 45 mins (first panel), treated with GFB-RA, followed by incubation with 500 nM HF-647-Aβ for 4 hrs and 75 nM Lysotracker for 45 mins (second panel), treated with GFB-RA, followed by incubation with 500 nM HF-647-Aβ for 4 hrs and washed in Aβ-free media for 6 hrs and incubated in 75 nM Lysotracker for 45 mins (third panel) and observed under microscope. Scale bar=20 μm. All data are representative of the mean±SEM of three independent experiments.

FIGS. 5 (A-F) illustrate that GFB and RA treatment increased lysosomal activity as well as autophagic flux: FIGS. 5(A-B) Mouse primary astrocytes were either untransfected, transfected with scrambled siRNA or Tfeb siRNA and treated with DMSO or GFB and RA. Whole cell extract was prepared and subjected to cathepsin assay for CtsB (A) and CtsD (B) (described in detail herein). FIG. 5(B) Whole cell extract from cells treated with DMSO or GFB-RA was used to perform immunoblot for the levels of CtsB and CtsD. FIG. 5(D) Densitometric analysis of the immunoblot, normalized to β-Actin. FIG. 5(E) Mouse primary astrocytes were treated with DMSO or GFB-RA, in presence of absence of 100 nM Bafilomycin A1, or 500 nM oligomeric Aβ. Whole cell extract was subjected to immunoblot for the levels of LC3 and p62. FIG. 5(F) Densitometric analysis of the immunoblot, normalized to β-Actin. p*<0.05 w.r.t control; ns-not significant. All data are representative of the mean±SEM of three independent experiments.

DETAILED DESCRIPTION OF THE PREFERRED EMBODIMENTS

Definitions

Figure 6:
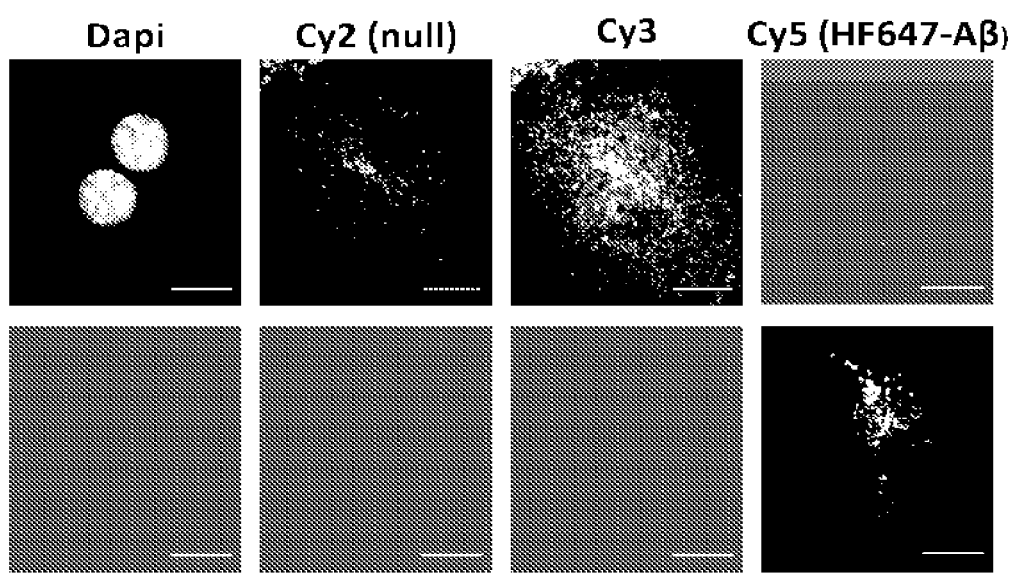
FIG. 6 shows a test for bleed through signals in different IF channels. Mouse primary astrocytes were cultured in DMEM/F12 media and stained separately with LysoTracker Red (top panel) and HF647-Aβ (bottom panel). Dapi is used to stain nuclei. The cells were observed under IF Microscope in DAPI, Cy2, Cy3 and Cy5 channels.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "therapeutic effect" as used herein means an effect which induces, ameliorates or otherwise causes an improvement in the pathological symptoms, disease progression or physiological conditions associated with or resistance to succumbing to a disorder, for example the aggregation of amyloid-β protein in the brain of a human or veterinary subject. The term "therapeutically effective amount" as used with respect to a drug means an amount of the drug which imparts a therapeutic effect to the human or veterinary patient.

Methods for Stimulating Clearance of Amyloid-β Protein

Alzheimer's disease is the most common human neurodegenerative disease, resulting in progressive neuronal death and memory loss. Neuropathologically, the disease is characterized by the presence of both neurofibrillary tangles and neuritic plaques composed of aggregates of amyloid-β (Aβ) protein, a 40-43 amino acid proteolytic fragment. In the Alzheimer's disease brain, while neurons die, glial cells like astrocytes and microglia do not die. Astrocytes are the major cell type in the brain, and may be utilized for breaking down amyloid plaques even in advanced Alzheimer's disease.

The administration of a composition including a therapeutically effective amount of an agonist of proliferator-activated receptor α ("PPARα") stimulates the uptake and degradation of amyloid-β (Aβ) in astrocytes. The composition may also include vitamin A or a derivative thereof. The agonist can be an amphipathic carboxylic acid. In certain embodiments the agonist is clofibrate, gemfibrozil, ciprofibrate, bezafibrate, clinofibrate or fenofibrate. In one preferred embodiment, the composition includes a combination of gemfibrozil and retinoic acid.

Gemfibrozil, an FDA-approved lipid-lowering, and vitamin A derivative retinoic acid stimulate the uptake and degradation of amyloid-β (Aβ) in astrocytes. Low density lipoprotein receptor (LDLR) plays an Important role in the uptake, whereas, TFEB mediated induction in lysosomal activity is critical for the degradation. Gemfibrozil and retinoic acid treatment also increased the autophagic flux and lysosomal activity in astrocytes as observed from increased LC3-11 formation and Increased cathepsin (B/D) activity, respectively.

Furthermore, the effect of gemfibrozil and retinoic acid on Aβ uptake/degradation is abrogated in absence of peroxisomal proliferator activated receptor α (PPARα), which plays a key role in gemfibrozil-retinoic acid mediated induction of TFEB. These results identify PPARα as an important regulator of astroglial uptake and degradation of Aβ via enhancement of lysosomal A(3 clearance and suggest that combination of vitamin A derivative retinoic acid and gemfibrozil or other PPARα agonists may reduce Aβ plaque load in Alzheimer's disease patients.

Gemfibrozil, an agonist of peroxisome proliferator-activated receptor α (PPARα) alone and in conjunction with all-trans-retinoic acid (RA) is capable of enhancing TFEB in brain cells. Retinoid X receptor (RXRα) and PPARα, but not PPARβ and PPARγ, are involved in GFB-mediated upregulation of TFEB. Reporter assay and chromatin immunoprecipitation studies confirmed the recruitment of RXRα, PPARα, and PPARγ co-activator 1α (PGC1α) on the PPAR binding site on Tfeb promoter. Subsequently, the drug mediated induction of TFEB caused increase in certain lysosomal proteins and the lysosomal proliferation in cell (14). These findings were in accordance with another study that also showed transcriptional regulation of TFEB by recruitment of PGC1α on TFEB promoter (15, 16).

Enhanced activity of lysosomes in Aβ uptake and degradation by mouse astrocytes was evaluated using an in vitro Aβ uptake and degradation assay, supported by microscopic observation of intracellular Aβ load. Significant increases were observed in both uptake and degradation of Aβ in WT and PPARβ(−/−), but not in PPARα(−/−) cells, when stimulated with GFB-RA. Silencing of LDLR by LDLR siRNA, reduced the rate of Aβ uptake, whereas gene silencing of TFEB, reduced the degradation rate. Furthermore, significant changes were observed in autophagic flux and lysosomal activity that could be mediated by GFB-RA treatment, by monitoring levels of Cathepsin B/D (CtsB/D), LC3-I/II and p62. Our data indicates that TFEB upregulation (and increase in lysosomal biogenesis) by PPARα: RXRα: PGC1α activation leads to increased uptake of Aβ and subsequent degradation of endocytosed Aβ in the lysosomes in mouse primary astrocytes.

Pharmaceutical Compositions

Another aspect of the present invention provides pharmaceutical compositions including an agent that is proliferator-activated receptor α ("PPARα") or an agonist of PPARα. In one embodiment, the agonist is an amphipathic carboxylic acid. For example, the agonist may be clofibrate, gemfibrozil, ciprofibrate, bezafibrate, clinofibrate or fenofibrate. Yet another aspect of the invention provides pharmaceutical compositions including a combination of an agent that is proliferator-activated receptor α ("PPARα") or an agonist of PPARα and vitamin A or a derivative thereof. In one preferred embodiment, the pharmaceutical composition includes gemfibrozil and retinoic acid.

The pharmaceutical compositions can be in the form of, for example, tablets, pills, dragees, hard and soft gel capsules, granules, pellets, aqueous, lipid, oily or other solutions, emulsions such as oil-in-water emulsions, liposomes, aqueous or oily suspensions, syrups, alixiers, solid emulsions, solid dispersions or dispersible powders. In pharmaceutical compositions for oral administration, the agent may be admixed with commonly known and used adjuvants and excipients, for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration the agent or pharmaceutical compositions of the agent can be in the form of an aqueous, lipid, oily or other kind of solution or suspension or even administered in the form of liposomes or nano-suspensions.

Modes of Administration

The pharmaceutical composition may be administered by any method that allows for the delivery of a therapeutic effective amount of the agent to the subject. Modes of administration can include, but are not limited to oral, topical, transdermal and parenteral routes, as well as direct injection into a tissue and delivery by a catheter. Parenteral routes can include, but are not limited to subcutaneous, intradermal, intra-articular, intravenous, intraperitoneal and intramuscular routes. In one embodiment, the route of administration is by topical or transdermal administration, such as by a lotion, cream, a patch, an injection, an implanted device, a graft or other controlled release carrier. Routes of administration include any route which directly delivers the composition to the systemic circulation (e.g., by injection), including any parenteral route. Alternatively, administration can be by delivery directly to the central nervous system.

One embodiment of the method of the invention includes administering the composition in a dose, concentration and for a time sufficient to prevent the development of, or to lessen the extent of Alzheimer's disease. In another embodiment, the invention includes administering the composition in a dose, concentration and for a time sufficient to reduce amyloid-β protein aggregates in the brain of a subject. In yet another embodiment, the invention includes administering the composition in a dose, concentration and for a time sufficient to stimulate the uptake of amyloid-β protein aggregates by astrocytes in the brain of a subject. In another embodiment, the invention includes administering the composition in a dose, concentration and for a time sufficient to stimulate degradation of amyloid-β protein aggregates by astrocytes in the brain of a subject.

Certain embodiments include administering systemically the composition in a dose between about 0.1 micrograms and about 100 milligrams per kilogram body weight of the subject, between about 0.1 micrograms and about 10 milligrams per kilogram body weight of the subject, between about 0.1 micrograms and about 1 milligram per kilogram body weight of the subject. In practicing this method, the composition can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

Embodiments of the invention will be further described in the following examples, which do not limit the scope of the invention described in the claims.

Example 1—Isolation of Primary Mouse Astroglia

Astroglia were isolated from mixed glial cultures as described (17,18) according to the procedure of Giulian and Baker (19). Briefly, on day 9, the mixed glial cultures were washed three times with Dulbecco's modified Eagle's medium/F-12 and subjected to shaking at 240 rpm for 2 h at 37° C. on a rotary shaker to remove microglia. After 2 days, the shaking was repeated for 24 h for the removal of oligodendroglia and to ensure the complete removal of all nonastroglial cells. The attached cells were seeded onto new plates for further studies.

Example 2—Semi-Quantitative Reverse Transcriptase-Coupled Polymerase Chain Reaction (RT-PCR)

Total RNA was isolated from mouse primary astrocytes and human primary astrocytes using RNA-Easy Qiagen kit following manufactures protocol. Semi-quantitative RT-PCR was carried out as described earlier (20) using oligo (dT) 12-18 as primer and moloney murine leukemia virus reverse transcriptase (MMLV-RT, Invitrogen) in a 20 μl reaction mixture. The resulting cDNA was appropriately amplified using Promega Master Mix and the primers for murine genes. Tfeb primer: Fwd: 5'-aacaaaggcaccatcctcaa-3' SEQ ID NO.: 1; Rev: 5'-cagctcggccatattcacac-3' SEQ ID NO.: 2 Ldlr primer was purchased from SantaCruz Biotechnology (Cat. No. sc-35803-PR). Amplified products were electrophoresed on 2% agarose gels and visualized by ethidium bromide staining. Glyceraldehyde-3-phosphate dehydrogenase (Gapdh) mRNA was used as a loading control to ascertain that an equivalent amount of cDNA was synthesized from each sample.

Example 3—Quantitative Real-Time PCR

The mRNA quantification was performed using the ABI-Prism7700 sequence detection system using SYBR Select master mix. The mRNA expression of the targeted genes was normalized to the level of Gapdh mRNA and data was processed by the ABI Sequence Detection System 1.6 software.

Example 4—Immunoblotting

Western blotting was conducted as described earlier (21, 22) with modifications. Briefly, cells were scraped in 1×RIPA buffer, protein was measured using Bradford reagent and sodium dodecyl sulfate (SDS) buffer was added and electrophoresed on NuPAGE® Novex® 4-12% Bis-Tris gels (Invitrogen) and proteins transferred onto a nitrocellulose membrane (Bio-Rad) using the Thermo-Pierce Fast Semi-Dry Blotter. The membrane was then washed for 15 min in TBS plus Tween 20 (TBST) and blocked for 1 hr in TBST containing BSA. Next, membranes were incubated overnight at 4° C. under shaking conditions with the following 1° antibodies; CtsB (Cell Signalling Technology, 1:1000), CtsD (Cell Signalling Technology, 1:1000), LC3 (Novus, 1:500), p62 (Abcam, 1:500) and β-actin (Abcam, 1:1000). The next day, membranes were washed in TBST for 1 hr, incubated in 2° antibodies against 1° antibody hosts (all 1:10,000; Jackson ImmunoResearch) for 1 hr at room temperature, washed for one more hour and visualized under the Odyssey® Infrared Imaging System (Li-COR, Lincoln, NE).

Example 5—Amyloid Beta Uptake Assay

Mouse primary astrocytes were plated in black 96-well plates. After appropriate treatment, the wells were incubated at 37° C. with 500 nM oligomeric FAM-tagged Aβ(1-42) for appropriate time-points. Finally the Aβ-containing medium was removed and wells were gently washed with normal media, followed by quenching of extracellular Aβ with 100 μl 0.2% trypan blue in PBS for 2 mins. After aspiration the fluorescence was measured Ex./Em. of 485/535 in Victor X2 microplate reader (Perkin Elmer). The wells were further incubated with 100 μl 50 μg/ml Hoechst 33342 dye in PBS for 30 mins and fluorescence was measured Ex./Em. of 360/465 nm (23). The Aβ fluorescence was normalized to Hoechst fluorescence to account for cell number variability if any.

Example 6—Amyloid Beta Degradation Assay

Mouse primary astrocytes were plated, treated and then incubated for 4 hrs with FAM-tagged Aβ(1-42). After incubation, Aβ containing media was removed and after a single gentle wash, the plates were incubated with normal media at 37° C. for different time points. The measurement of Aβ and Hoechst fluorescence was measure as mentioned above.

Example 7—Immunocytochemistry for Amyloid Beta Uptake/Degradation

Mouse primary astrocytes were cultured on square coverslips placed in 6 well plates. After treatment cells were incubated with 500 nM of oligomeric HF-647-tagged Aβ(1-

42). For degradation study, the cells were further allowed to grow in normal media, after removal of Aβ containing media. After incubation, cells were further incubated in media containing 75 nM LysoTracker Red DND99 for 30 mins. The cells were then washed, fixed on glass slides and observed under BX41 fluorescence microscope (23).

Example 8—Cathepsin Assay

Mouse primary astrocytes were cultured, treated and lysed in 100 mm sodium acetate, pH 5.5, with 2.5 mm EDTA, 0.01% Triton X-100, and 2.5 mm DTT.

For Cathepsin B assay, the supernatant was incubated for 30 mins at pH 6.0 with 100 μM Z-Arg-Arg-AMC. 7-amino-4-methylcoumarin, AMC was used as standard. The fluorescence was measured at Ex./Em. of 355/460 nm in Victor X2 microplate reader.

For Cathepsin D assay, the supernatant was incubated 10 μM substrate 7-methoxycoumarin-4-acetyl-(Mca)-Gly-Lys-Pro-Ile-Leu-Phe-Phe-Arg-Leu-Lys-2,4 nitrophenyl (Dnp)-D-Arg-NH$_2$ at pH 4.0 for 30 mins. Mca-Pro-Leu-OH was used as standard. The fluorescence was measured at Ex./Em. of 320/420 nm.

The fluorescence readings of the samples were compared to the respective standard to measure the amount of product obtained. Cathepsin activity (in Units) was calculated per mg of cell extract, considering 1 Unit of enzyme activity released 1 nmole of product per hour at 37° C. (24,25).

Example 9—Densitometric Analysis

Protein blots were analyzed using ImageJ (NIH, Bethesda, MD) and bands were normalized to their respective β-actin loading controls. Immunofluorescence quantification data are representative of the average fold change with respect to control for at least 25 different images per condition from three independent set of experiments.

Example 10—Statistical Analysis

Values are expressed as means±SEM of at least three independent experiments. Statistical analyses for differences were performed via Student's T-test. This criterion for statistical significance was $p<0.05$.

Example 11—GFB and RA Treatment Enhancement of Aβ Uptake in Mouse Primary Astrocytes Lysosomal activity is crucial for the clearance of Aβ in the Alzheimer's disease brain. Therefore, we explored the effect of GFB and RA, which enhances lysosomal biogenesis, on the uptake of extracellular Aβ by mouse primary astrocytes. We performed both quantitative in vitro assay and qualitative microscopic analysis to measure the alterations in the levels of Aβ in taken up by the cells.

The in vitro assay is a robust technique that can quantitatively measure the signal intensity of FAM-tagged Aβ(1-42) from inside the cell. The cells were treated with GFB-RA and further incubated with FAM-Aβ(1-42) for various time points (15', 30', 45', 1 hr, 2 hr, 4 hr and 8 hr). The signal intensity of Aβ was first normalized to that of Hoechst, to account for the variability in cell number in each well, if any. Then the normalized Aβ signals of GFB-RA treated samples were compared to their DMSO treated counterparts and percentage change in the Aβ signal was calculated for each time point.

After 2 hrs of incubation in Aβ containing media, the amount of Aβ inside the GFB-RA treated cells were ~60% more compare to the DMSO treated cells. At 4 hrs, the Aβ signal in treated cells were about ~80% higher than the control (FIG. 1A). However further incubation up to 8 hrs did not yield any further increase in the Aβ content in treated cells, indicating that 4 hrs of incubation would be the optimum time point for the assay. Therefore, for further uptake assays, this time point of Aβ incubation was selected.

Fluorescence microscopy was performed by incubating the cells with HF-647-tagged Aβ(1-42) for 2 hrs and 4 hrs followed by incubation with LysoTracker Red. We observed increased punctate signal of HF-647-Aβ in both 2 hrs and 4 hrs in GFB-RA treated cells compared to DMSO control. Furthermore, the Aβ signal co-localized with the LysoTracker signal, indicating that the Aβ taken up by the cells were residing in the acidic vesicles inside the cell (late endosomes or lysosomes) (FIG. 1B). Since the patterns of Aβ signal and LysoTracker signal were expected to be similar, we incubated cells separately with LysoTracker and HF-647-Aβ and tested all channels for any bleed through signals. As expected, only LysoTracker showed slight signal overlap between CY2 and CY3 channels, but there was no significant bleed through signal in any other channel for HF-647-Aβ apart from its true signal in CY5 channel (FIG. 6).

Example 12—Effect of LDLR and TFEB on GFB-RA Mediated Uptake of Aβ

Aβ could be taken up through micropinocytosis assisted by heparan sulfate proteoglycans (HSPGs) (26). Therefore, to elucidate the mechanism of GFB-RA mediated enhancement of Aβ uptake, we performed Aβ uptake assay in presence of Heparin (inhibitor of HSPGs) first. Cells treated with GFB-RA in presence of heparin showed ~40% increase in Aβ uptake compare to ~80% in GFB-RA treated cells in absence of heparin (FIG. 2A). Although, this reduction in the uptake level is statistically significant, but still there was about 40% uptake even in presence of heparin, which indicates that other factors may also be responsible for the uptake process. We transfected the cells with Tfeb siRNA, and observed slight decrease (not statistically significant, p=0.59) in the uptake level of Aβ in Tfeb siRNA transfected cells compared to scrambled siRNA transfected cells (FIG. 2B). The efficacy of TFEB silencing is shown in FIG. 2D. These data further enforced the idea that neither HSPGs nor TFEB alone is responsible for the enhance uptake of Aβ. Recent reports suggest that lipoprotein receptors like LDLR and LRP1 also facilitate the internalization of Aβ in glial cells. Interestingly, there are reports that hepatic expression of LDLR is induced by fenofibrate (FF) by a PPARα dependent mechanism involving Akt phosphorylation and transcriptional activation of SREBP2 (27,28). Therefore, we further transfected cells with Ldlr siRNA and observed that the effect of GFB-RA on Aβ uptake is attenuated in absence of LDLR (FIG. 2B). The efficiency of LDLR silencing is evident from FIG. 2C. Also, treatment with GFB, a fibrate, along with RA induced the expression of LDLR in WT astrocytes, but not in PPARα(−/−) cells (FIG. 2C). Taken together, this set of data, indicates that GFB-RA promotes uptake of Aβ in astrocytes via LDLR mediated endocytosis.

Example 13—GFB and RA Treatment Enhances Degradation of Aβ in Mouse Primary Astrocytes We have observed colocalization of Aβ with the LysoTracker, a lysosomal dye (FIG. 1B). So it is imperative that there will be degradation of Aβ inside the lysosome, provided there is proper functioning of the organelle. We wanted to observe, whether induction of TFEB (and subsequent induction of lysosomal genes & lysosomal biogenesis) could accelerate the process of degradation Aβ in the lysosome. We deployed the same in vitro assay for intracellular Aβ content, but this time, after incubation with Aβ for 4 hrs, the cells were allowed to grow for different time points (15', 30', 1 hr, 2 hr, 4 hr, 6 hr and 8 hr) in Aβ-free media. The normalized Aβ signal (normalized to Hoechst signal) for DMSO treated cells and GFB-RA treated cells were compared to their respective counterparts which were not allowed to grow in Aβ free media (termed as "0 min wash"). As expected, the basal level of lysosomal processing of Aβ caused reduction in signal intensity of intracellular Aβ by ~20% within 6-8 hrs compared to 0' wash cells. On the other hand, cells treated with GFB-RA showed an accelerated clearance rate, with a reduction of signal by ~40% within 6-8 hrs (FIG. 3A). The data showed optimal degradation at 6 hrs, hence that time point was used for further degradation assays (termed as "6 hr wash"). We also visualized reduced puncta of HF-647-Aβ after 6 hrs of wash under the microscope (FIG. 3B). To determine whether the loss of Aβ signal was due to lysosomal processing, we incubated the cells with Bafilomycin A1 (BafA1) that inhibits lysosomal acidification, thereby reducing its activity. The presence of BafA1 arrested the accelerated loss of Aβ as observed in GFB-RA treated cells, and rate of Aβ degradation was almost similar in both DMSO and GFB-RA treated cells, in presence of BafA1 (FIG. 3C). Furthermore, transfection of cells with Tfeb siRNA also attenuated the GFB-RA mediated accelerated lysosomal degradation of Aβ (FIG. 3D). Collectively, these data indicates that, GFB-RA treatment mediated induction of lysosomal biogenesis could accelerate the process of lysosomal Aβ degradation.

Example 14—Role of PPARα and PPARβ in GFB-RA Mediated Aβ Uptake and Degradation

PPARα plays a key role mediating the transcriptional activation of TFEB and subsequent enhancement in lysosomal biogenesis. We tested the absence of PPARα and PPARβ affects the regulation of Aβ uptake and degradation in mouse primary astrocytes. Cells isolated from WT, PPARα(−/−) and PPARβ(−/−) animals were treated with GFB and RA and further incubated with FAM-Aβ(1-42) (for in vitro assay) and HF-647-Aβ along with LysoTracker Red (for microscopy). As before, the Aβ signals were normalized to Hoechst signal to account for any variability in cell number.

The Aβ uptake assay, after 4 hrs of incubation with Aβ, showed prominent increase in the Aβ content (measured by FAM-Aβ signal intensity) inside the cell, in both WT and PPARβ(−/−) cells, but not in PPARα(−/−) (FIG. 4A). The signal intensity for all cells was compared to DMSO-treated WT controls. Although there was a slight increase in the levels of Aβ in PPARα(−/−) cells treated with GFB-RA (~20%), it was not significant compared to the ~80% and ~70% increase in GFB-RA treated WT and PPARβ(−/−) cells, respectively (FIG. 4A). In order the assess the role of PPARs in Aβ degradation, the cells from WT and both knockout animals were treated, incubated with Aβ and further allowed to grow in Aβ-free media for 6 hrs. The normalized Aβ signal for GFB-RA treated astrocytes for each of the cell types, either with or without the 6 hr wash, were first compared to their respective DMSO-treated controls. Then percentage change of intracellular Aβ signals in 6 hr washed GFB-RA treated cells (previously normalized to their DMSO treated controls) were calculated with respect to 0 min washed GFB-RA treated cells (previously normalized to their DMSO-treated controls) for each cell types. We observed ~60% reduction in the levels of Aβ both in WT and PPARβ(−/−) cells, but only 30-35% loss in signal in case of PPARα(−/−) (FIG. 4B). Although, as observed earlier, Aβ was differentially taken up by these three cell types, but comparing the percentage change with respect to Aβ content pre- and post-6 hr wash (derivations described in detail in Discussion), accounted for the variability of Aβ uptake and provided an absolute measure for Aβ degradation.

Furthermore, the observations from microscopy, also revealed reduced signal intensity of both Aβ and LysoTracker in PPARα(−/−) cells compared to PPARβ and WT cells (FIGS. 4C, 4D & 4E). This was in agreement with our previous finding that absence of PPARα abrogates the GFB-RA mediated enhancement of lysosomal proliferation as well as attenuates the expression of LDLR, a key component of Aβ uptake.

Microscopic analysis also revealed reduced puncta of HF-647-Aβ in WT and PPARβ(−/−) post 6 hr wash, but not a significant change in PPARα(−/−) cells (FIGS. 4C, 4D & 4E). Collectively, these data indicate that PPARα has a dual role—by regulating the expression of LDLR, it could facilitate the uptake Aβ and by enhancing lysosomal biogenesis via TFEB, it induces accelerated degradation of Aβ in the lysosomes.

Example 15—GFB and RA Treatment Enhanced Lysosomal Activity and Autophagic Flux

The enhancement of lysosomal degradation of Aβ led us to investigate the markers for lysosomal activity and autophagy. We assessed the GFB-RA treatment on cathepsin B (CtsB) & cathepsin D (CtsD), the two important cathepsins involved in degradation of Aβ fragments in the lysosomes. The cathepsin activity assay was performed as described in Materials and methods, in cells treated with GFB-RA both in presence and absence of Tfeb siRNA, to determine whether any alteration in the activity due to GFB-RA treatment is mediated via TFEB. Our data indicates an increase in the activity both the cathepsins upon treatment with GFB-RA. Silencing of TFEB by siRNA abrogated the effect of the drugs on cathepsins activity (FIGS. 5A & 5B). The protein levels of both cathepsins were found to increase by about 2-3 fold in cells treated with GFB-RA (FIGS. 5C & 5D). This is in accordance with the findings that CtsB and CtsD are direct targets of TFEB and enhancement of TFEB activity subsequently induces the levels and activity of cathepsins as well.

It has been reported that deficiency in autophagy or blockage of autophagic pathway, result in abnormal accumulation of Aβ in autophagic vacuoles inside the cell and is one of the main cause for Aβ induced neurotoxicity (9). Therefore, we observed the changes in autophagic flux in GFB-RA treated cells, by monitoring the levels of LC3 (LC3-I/LC3-II) and p62/SQSTM1. GFB-RA treatment increased the levels of the LC3-II, the phosphatidylethanolamine conjugated form of LC3-I (FIGS. 5E & 5F). The conversion of LC3-I to LC3-II is a hallmark of autophagy induction. We further blocked lysosomal activity by using BafA1 and observed further accumulation of LC3-II (FIGS. 5E & 5F). In accordance of previous studies, we also observed reduced levels of p62 in conditions where there is accumulation of LC3-II, further enforcing the enhancement of autophagic flux (FIGS. 5E & 5F).

Taken together, these data validates our hypothesis, that increase in lysosomal biogenesis via TFEB, mediated by GFB-RA, in a PPARα-dependent manner could induce the Aβ uptake and subsequent degradation in the lysosomes by mouse primary astrocytes.

Example 16—Discussion of Experimental Protocols

The role of lysosomal activity in Aβ production, uptake and clearance has been well established in the past few years (1, 2, 7, 11, 23). Here, we observed the enhanced lysosomal biogenesis by GFB-RA in Aβ uptake and degradation by mouse primary astrocytes. An in vitro assay using FAM-tagged Aβ(1-42) was performed in 96-well microplates, allowing for assessment of multiple samples/treatment at the same time. Only intracellular Aβ signal from live cells are detected at 485/535 nm (Ex./Em.) by quenching the extracellular signal and signal from dead cells by using Trypan blue. Furthermore, normalizing the Aβ signal with Hoechst 33342 signal from the same well at 360/465 nm accounts for the cell number variability.

Depending on the type of experiment, the data can be compared to appropriate controls and represented as fold change or percentage change of the Aβ uptake/degradation. WT and PPARβ(−/−) cells showed significant increase in Aβ uptake upon treatment, whereas PPARα(−/−) cell did not show much increase. The co-localization of HF-647-Aβ signal and LysoTracker observed under microscope showed that internalized Aβ indeed ended up in the lysosomes. The reduced intracellular Aβ signal in presence of Heparin and LDLR siRNA indicated the role of HSPGs and LDLR in micropinocytosis and endocytosis of extracellular Aβ by astrocytes. Although the link between PPARα or TFEB activation with micropinocytosis is not fully understood, it appears that increased lysosomal biogenesis enhances the turnover of pinocytic vesicle, thereby resulting in increased HSPGs mediated uptake of Aβ.

The role of LDLR in Aβ uptake and degradation has been well established. Previous studies showed that overexpression of LDLR inhibited Aβ deposition and enhanced clearance of extracellular Aβ (29). The effect could be mediated with or without the involvement of Apolipoprotein E (ApoE), one of the strongest genetic risk factors for Alzheimer's disease (27-29). Furthermore, LDLR overexpression has been also shown to facilitate the rate of brain-to-blood transport of cerebral Aβ, thereby enhancing clearance of pathologic Aβ from brain (30). Also, when LDLR is deleted in 5×FAD mouse model of Alzheimer's disease (5×FAD/LDLR−/−), there was evidence of increased amyloid beta deposition and reduced glial inflammatory response, which indicate the role the LDLR in gliosis and Aβ clearance, independent of ApoE (31). Interestingly, expression of LDLR, another candidate for Aβ uptake is also regulated via SREBP2 by activation of PPARα. Fenofibrate (FF), another fibrate that belongs to the same class as gemfibrozil has been shown to upregulate hepatic LDLR expression in a PPARα-SREBP2 mediated pathway (32). In our study treatment with GFB, which is a well known activator of PPARα, also increased LDLR expression in WT cells but not in PPARα(−/−) cells. Also, knockdown of LDLR in astrocytes, attenuated the enhancement of Aβ uptake. Based on this data, we revealed a novel role of PPARα (as well as its activator, GFB) in facilitating the uptake of Aβ in vitro in mouse primary astrocytes in LDLR-dependent manner.

The degradation assay was also performed in similar fashion. Only this time, the cells were allowed to grow in Aβ-free media for various time points prior to the measurement of signal. Inhibition of lysosomal activity by BafA1 or silencing of TFEB showed reduced degradation of Aβ, which reinforced the role of lysosome in degradation of Aβ(1-42). However, when we assayed for Aβ degradation in WT, PPARα(−/−) and PPARβ(−/−) cells, the calculations were a bit more complicated. In this case, we had three different cell types (WT, PPARα(−/−) and PPARβ(−/−)) which respond differentially to GFB-RA treatment in terms of Aβ uptake. So, for proper assessment of degradation, the levels of Aβ, post 6 hr wash, had to be compared with the fold change in Aβ prior to wash (0′ wash), individually, for each type of GFB-RA treated cells.

$1^{st}$ Order Derivation:

Aβ signal normalized to Hoechst signal=$Aβ_{norm}$ (for all conditions)

$2^{nd}$ Order Derivation:

$Aβ_{norm}$(Tx,0′ wash) normalized to $Aβ_{norm}$(DMSO,0′ wash)=$Aβ_{fold}$(Tx, 0′ wash)

$Aβ_{norm}$(Tx,6 hr wash) normalized to $Aβ_{norm}$ (DMSO,6 hr wash)=$Aβ_{fold}$(Tx,6 hr wash)

$3^{rd}$ Order Derivation:

{$Aβ_{fold}$(Tx,6 hr wash)/$Aβ_{fold}$(Tx,0′ wash)}*100=% change

This third order derivation of the Aβ signal allowed us to compare between the net reduction in Aβ content in the cell compared to the net uptake of Aβ by the same cells prior to wash.

Finally, the activity of lysosome was measured by monitoring the activity of two of its hydrolases, Cathepsin B and D. CtsB and CtsD are two well-known direct targets of TFEB, so as expected we observed increased activity and levels of the enzymes. In the endosomal-lysosomal pathway of Aβ production, the beta-amyloid fragments generated by lysosomal hydrolases are subsequently degraded by the cathepsins (CtsB & D) (8). Inhibition of cathepsins cause a rapid buildup of Aβ fragments, on the other hand it has been shown that increased cathepsin activity results in effective degradation of Aβ and reduction in Aβ plaques (33). Also, it has been shown that enhanced autophagy results in lysosomal degradation of Aβ and protects neurons from Aβ induced neurotoxicity (34).

Abnormal or improper processing of Aβ by autophagic process also causes secretion of toxic Aβ fragments to extracellular space and deficiency in autophagy results in accumulation of Aβ in lysosomes, thereby causing LMP (13). Therefore, we also checked the alteration in autophagic flux by monitoring the conversion of LC3-I to LC3-II and its associated protein p62. Microtubule associated protein 1 (MAP1) light chain 3 (MAP-LC3 or simply LC3) exists as a free soluble form (LC3-I), which is covalently conjugated to phosphatidylethanolamine (LC3-II) by the enzymatic action of Atg4 (35,36). Signals leading to induction of autophagy trigger the conversion. LC3-II remains bound to the autophagosome membrane and is essential for the de novo production of autophagic vacuole (37,38). Monitoring the changes in the levels of LC3-I/II is considered to be a simple and effective way to monitor autophagy induction (10). However, mere increase in the levels of LC3-II does not necessarily indicate complete autophagy. LC3-II itself is degraded in the later stages of autophagic degradation, which makes the interpretation of LC3 immunoblot results more complex.

Therefore, monitoring LC3-I/II levels both in presence of activators and inhibitors of autophagy has been proposed to be a better way to interpret the data (39,40). The increased accumulation of LC3-II under lysosomal inhibitory condition is due to constant increase of autophagic flux, but reduced clearance of LC3-II by lysosomal degradation. On the other hand, another marker for autophagy, p62, also known as sequestsome1 (SQSTM1), which delivers LC3-II to the autophagosome and majority of p62, is degraded in the early stages of autophagosome formation (39-42). The expected negative correlation of p62 and LC3, as observed in our data as well as by other groups, indicated increased autophagic flux in cells treated with GFB-RA.

The role of autophagy in APP processing, Aβ production and degradation has been extensively studied. The endosomal-lysosomal pathway of APP processing, as discussed earlier, contributes significantly in regulating the generation of pathologic Aβ fragments (7,9). Because APP is processed in the lysosomes, disruption of lysosomal function as well as suppression of Aβ degradation and secretion results in accumulation of intra- and extra-lysosomal Aβ (43,44). In neuroblastoma cell line, N2a, inhibition of glycogen synthase kinase 3 (GSK3) promotes lysosomal biogenesis and facilitate Aβ degradation in lysosomes (45). Also, LDLR-related protein 1 (LRP1) mediates Aβ internalization and degradation in neurons (46,47). A wide array of receptors, like complement receptor 1 (CR1), scavenger receptors (SR-A), CD36, receptor for advanced glycosylation end-products (RAGE), toll-like receptors (TLRs), transforming growth factor beta1 (TGF-beta1), triggering receptor expressed on myeloid cells 2 (TREM2), etc. has been identified on the surface of microglia that interacts with extracellular Aβ and induces signalling mechanisms leading to Aβ uptake and degradation (48-51). The role of astrocytes in Aβ clearance and degradation is also considered beneficial, as astrocytes internalize ApoE-Aβ complexes from extracellular space and subsequently degrades them or secretes them in perivascular spaces (52-54). Astrocytes are also capable of degrading Aβ by enzymatic action of NEP, matrix metalloproteinase-9 (MMP-9), or insulin-degrading enzyme (IDE) (55-60). However, prolonged exposure to pathologic Aβ, renders astrocytes incapable of handling such huge amount of Aβ cargo and results in Aβ accumulation in astrocytes (61,62). In the past few years, enhancement of lysosomal biogenesis has been shown to play a critical role in Aβ internalization and degradation. Adeno-associated virus (AAV) carrying TFEB gene driven by glial fibrilary acidic protein (GFAP) promoter or CMV-promoter was administered by stereotactic injection into hippocampus of APP/PS1 mice, which are specifically targeted to astrocytes or neurons, respectively. TFEB overexpression leads to induction in lysosomal biogenesis and eventually results in enhanced uptake and clearance of Aβ from the interstitial fluids by astrocytes and enhanced processing of APP by neurons, that reduces Aβ production (23,63). These studies underscore the importance of astrocytic clearance of Aβ in Alzheimer's disease, however, drug mediated enhancement of Aβ clearance by inducing lysosomal biogenesis has not been well studied so far.

In summary, activation of PPARα by fibrates leads to enhanced uptake and clearance of Aβ by mouse primary astrocytes. The outcome of this investigation highlights previously unknown properties of PPARα, provides a new treatment option for Alzheimer's disease, as well as lysosomal storage disease, and reveals a more dynamic regulation of TFEB.

REFERENCES

1. Takahashi, R. H., Capetillo-Zarate, E., Lin, M. T., Milner, T. A., and Gouras, G. K. Co-occurrence of Alzheimer's disease ss-amyloid and tau pathologies at synapses. *Neurobiol Aging* 31, 1145-1152
2. Li, M., Chen, L., Lee, D. H., Yu, L. C., and Zhang, Y. (2007) The role of intracellular amyloid beta in Alzheimer's disease. *Prog Neurobiol* 83, 131-139
3. Citron, M., Teplow, D. B., and Selkoe, D. J. (1995) Generation of amyloid beta protein from its precursor is sequence specific. Neuron 14, 661-670
4. Okochi, M., Eimer, S., Bottcher, A., Baumeister, R., Romig, H., Walter, J., Capell, A., Steiner, H., and Haass, C. (2000) A loss of function mutant of the presenilin homologue SEL-12 undergoes aberrant endoproteolysis in *Caenorhabditis elegans* and increases abeta 42 generation in human cells. *J Biol Chem* 275, 40925-40932
5. Capell, A., Steiner, H., Willem, M., Kaiser, H., Meyer, C., Walter, J., Lammich, S., Multhaup, G., and Haass, C. (2000) Maturation and pro-peptide cleavage of beta-secretase. *J Biol Chem* 275, 30849-30854
6. Vetrivel, K. S., Zhang, Y. W., Xu, H., and Thinakaran, G. (2006) Pathological and physiological functions of presenilins. *Mol Neurodegener* 1, 4
7. Vetrivel, K. S., and Thinakaran, G. (2006) Amyloidogenic processing of beta-amyloid precursor protein in intracellular compartments. *Neurology* 66, S69-73
8. Bagnoli, S., Nacmias, B., Tedde, A., Guarnieri, B. M., Cellini, E., Ciantelli, M., Petruzzi, C., Bartoli, A., Ortenzi, L., Serio, A., and Sorbi, S. (2002) Cathepsin D polymorphism in Italian sporadic and familial Alzheimer's disease. *Neurosci Lett* 328, 273-276
9. Nixon, R. A. (2007) Autophagy, amyloidogenesis and Alzheimer disease. *J Cell Sci* 120, 4081-4091
10. Klionsky, D. J., Abeliovich, H., Agostinis, P., Agrawal, D. K., Aliev, G., Askew, D. S., Baba, M., Baehrecke, E. H., Bahr, B. A., Ballabio, A., Bamber, B. A., Bassham, D. C., Bergamini, E., Bi, X., Biard-Piechaczyk, M., Blum, J. S., Bredesen, D. E., Brodsky, J. L., Brumell, J. H., Brunk, U. T., Bursch, W., Camougrand, N., Cebollero, E., Cecconi, F., Chen, Y., Chin, L. S., Choi, A., Chu, C. T., Chung, J., Clarke, P. G., Clark, R. S., Clarke, S. G., Clave, C., Cleveland, J. L., Codogno, P., Colombo, M. I., Coto-Montes, A., Cregg, J. M., Cuervo, A. M., Debnath, J., Demarchi, F., Dennis, P. B., Dennis, P. A., Deretic, V., Devenish, R. J., Di Sano, F., Dice, J. F., Difiglia, M., Dinesh-Kumar, S., Distelhorst, C. W., Djavaheri-Mergny, M., Dorsey, F. C., Droge, W., Dron, M., Dunn, W. A., Jr., Duszenko, M., Eissa, N. T., Elazar, Z., Esclatine, A., Eskelinen, E. L., Fesus, L., Finley, K. D., Fuentes, J. M., Fueyo, J., Fujisaki, K., Galliot, B., Gao, F. B., Gewirtz, D. A., Gibson, S. B., Gohla, A., Goldberg, A. L., Gonzalez, R., Gonzalez-Estevez, C., Gorski, S., Gottlieb, R. A., Haussinger, D., He, Y. W., Heidenreich, K., Hill, J. A., Hoyer-Hansen, M., Hu, X., Huang, W. P., Iwasaki, A., Jaattela, M., Jackson, W. T., Jiang, X., Jin, S., Johansen, T., Jung, J. U., Kadowaki, M., Kang, C., Kelekar, A., Kessel, D. H., Kiel, J. A., Kim, H. P., Kimchi, A., Kinsella, T. J., Kiselyov, K., Kitamoto, K., Knecht, E., Komatsu, M., Kominami, E., Kondo, S., Kovacs, A. L., Kroemer, G., Kuan, C. Y., Kumar, R., Kundu, M., Landry, J., Laporte, M., Le, W., Lei, H. Y., Lenardo, M. J., Levine, B., Lieberman, A., Lim, K. L., Lin, F. C., Liou, W., Liu, L. F., Lopez-Berestein, G., Lopez-Otin, C., Lu, B., Macleod, K. F., Malorni, W., Martinet, W., Matsuoka, K., Mautner, J., Meijer, A. J., Melendez, A., Michels, P., Miotto, G., Mistiaen, W. P., Mizushima, N., Mograbi, B., Monastyrska, I., Moore, M. N., Moreira, P. I., Moriyasu, Y., Motyl, T., Munz, C., Murphy, L. O., Naqvi, N. I., Neufeld, T. P., Nishino, I., Nixon, R. A., Noda, T., Nurnberg, B., Ogawa, M., Oleinick, N. L., Olsen, L. J., Ozpolat, B., Paglin, S., Palmer, G. E., Papassideri, I., Parkes, M., Perlmutter, D. H., Perry, G., Piacentini, M., Pinkas-Kramarski, R., Prescott, M., Proikas-Cezanne, T., Raben, N., Rami, A., Reggiori, F., Rohrer, B., Rubinsztein, D. C., Ryan, K. M., Sadoshima, J., Sakagami, H., Sakai, Y., Sandri, M., Sasakawa, C., Sass, M., Schneider, C., Seglen, P. O., Seleverstov, O., Settleman, J., Shacka, J. J., Shapiro, I. M., Sibirny, A., Silva-Zacarin, E. C., Simon, H. U., Simone, C., Simonsen, A., Smith, M. A., Spanel-Borowski, K., Srinivas, V., Steeves, M., Stenmark, H., Stromhaug, P. E., Subauste, C. S., Sugimoto, S., Sulzer, D., Suzuki, T., Swanson, M. S., Tabas, I., Takeshita, F., Talbot, N. J., Talloczy, Z., Tanaka, K., Tanida, I., Taylor, G. S., Taylor, J. P., Terman, A., Tettamanti, G., Thompson, C. B., Thumm, M., Tolkovsky, A. M., Tooze, S. A., Truant, R., Tumanovska, L. V., Uchiyama, Y., Ueno, T., Uzcategui, N. L., van der Klei, I., Vaquero, E. C., Vellai, T., Vogel, M. W., Wang, H. G., Webster, P., Wiley, J. W., Xi, Z., Xiao, G., Yahalom, J., Yang, J. M., Yap, G., Yin, X. M., Yoshimori, T., Yu, L., Yue, Z., Yuzaki, M., Zabirnyk, O., Zheng, X., Zhu, X., and Deter, R. L. (2008) Guidelines for the use and interpretation of assays for monitoring autophagy in higher eukaryotes. *Autophagy* 4, 151-175

11. Mueller-Steiner, S., Zhou, Y., Arai, H., Roberson, E. D., Sun, B., Chen, J., Wang, X., Yu, G., Esposito, L., Mucke, L., and Gan, L. (2006) Antiamyloidogenic and neuroprotective functions of cathepsin B: implications for Alzheimer's disease. *Neuron* 51, 703-714

12. Zhang, L., Sheng, R., and Qin, Z. (2009) The lysosome and neurodegenerative diseases. *Acta Biochim Biophys Sin (Shanghai)* 41, 437-445

13. Ditaranto, K., Tekirian, T. L., and Yang, A. J. (2001) Lysosomal membrane damage in soluble Abeta-mediated cell death in Alzheimer's disease. *Neurobiol Dis* 8, 19-31

14. Ghosh, A., Jana, M., Modi, K., Gonzalez, F. J., Sims, K. B., Berry-Kravis, E., and Pahan, K. Activation of peroxisome proliferator-activated receptor alpha induces lysosomal biogenesis in brain cells: implications for lysosomal storage disorders. *J Biol Chem* 290, 10309-10324

15. Tsunemi, T., and La Spada, A. R. PGC-1alpha at the intersection of bioenergetics regulation and neuron function: from Huntington's disease to Parkinson's disease and beyond. *Prog Neurobiol* 97, 142-151

16. Tsunemi, T., Ashe, T. D., Morrison, B. E., Soriano, K. R., Au, J., Roque, R. A., Lazarowski, E. R., Damian, V. A., Masliah, E., and La Spada, A. R. (2012) PGC-1alpha rescues Huntington's disease proteotoxicity by preventing oxidative stress and promoting TFEB function. *Sci Transl Med* 4, 142ra197

17. Brahmachari, S., and Pahan, K. (2007) Sodium benzoate, a food additive and a metabolite of cinnamon, modifies T cells at multiple steps and inhibits adoptive transfer of experimental allergic encephalomyelitis. *J Immunol* 179, 275-283

18. Saha, R. N., and Pahan, K. (2007) Differential regulation of Mn-superoxide dismutase in neurons and astroglia by HIV-1 gp120: Implications for HIV-associated dementia. *Free Radic Biol Med* 42, 1866-1878

19. Giulian, D., and Baker, T. J. (1986) Characterization of ameboid microglia isolated from developing mammalian brain. *J Neurosci* 6, 2163-2178

20. Khasnavis, S., Jana, A., Roy, A., Wood, T., Ghosh, S., Watson, R., and Pahan, K. Suppression of nuclear factor-kappa B activation and inflammation in microglia by a physically-modified saline. *J Biol Chem*

21. Corbett, G. T., Roy, A., and Pahan, K. Gemfibrozil, a Lipid-Lowering Drug, Upregulates IL-1 Receptor Antagonist in Mouse Cortical Neurons: Implications for Neuronal Self-Defense. *J Immunol* 189, 1002-1013

22. Saha, R. N., Liu, X., and Pahan, K. (2006) Up-regulation of BDNF in astrocytes by TNF-alpha: a case for the neuroprotective role of cytokine. *J Neuroimmune Pharmacol* 1, 212-222

23. Xiao, Q., Yan, P., Ma, X., Liu, H., Perez, R., Zhu, A., Gonzales, E., Burchett, J. M., Schuler, D. R., Cirrito, J. R., Diwan, A., and Lee, J. M. Enhancing astrocytic lysosome biogenesis facilitates Abeta clearance and attenuates amyloid plaque pathogenesis. *J Neurosci* 34, 9607-9620

24. Bond, J. S., and Barrett, A. J. (1980) Degradation of fructose-1,6-bisphosphate aldolase by cathepsin B. *Biochem J* 189, 17-25

25. Barrett, A. J. (1980) Fluorimetric assays for cathepsin B and cathepsin H with methylcoumarylamide substrates. *Biochem J* 187, 909-912

26. van Horssen, J., Wesseling, P., van den Heuvel, L. P., de Waal, R. M., and Verbeek, M. M. (2003) Heparan sulphate proteoglycans in Alzheimer's disease and amyloid-related disorders. *Lancet Neurol* 2, 482-492

27. Basak, J. M., Verghese, P. B., Yoon, H., Kim, J., and Holtzman, D. M. Low-density lipoprotein receptor represents an apolipoprotein E-independent pathway of Abeta uptake and degradation by astrocytes. *J Biol Chem* 287, 13959-13971

28. Basak, J. M., Kim, J., Pyatkivskyy, Y., Wildsmith, K. R., Jiang, H., Parsadanian, M., Patterson, B. W., Bateman, R. J., and Holtzman, D. M. Measurement of apolipoprotein E and amyloid beta clearance rates in the mouse brain using bolus stable isotope labeling. *Mol Neurodegener* 7, 14

29. Kim, J., Castellano, J. M., Jiang, H., Basak, J. M., Parsadanian, M., Pham, V., Mason, S. M., Paul, S. M., and Holtzman, D. M. (2009) Overexpression of low-density lipoprotein receptor in the brain markedly inhibits amyloid deposition and increases extracellular A beta clearance. *Neuron* 64, 632-644

30. Castellano, J. M., Deane, R., Gottesdiener, A. J., Verghese, P. B., Stewart, F. R., West, T., Paoletti, A. C., Kasper, T. R., DeMattos, R. B., Zlokovic, B. V., and Holtzman, D. M. Low-density lipoprotein receptor overexpression enhances the rate of brain-to-blood Abeta clearance in a mouse model of beta-amyloidosis. *Proc Natl Acad Sci USA* 109, 15502-15507

31. Katsouri, L., and Georgopoulos, S. Lack of LDL receptor enhances amyloid deposition and decreases glial response in an Alzheimer's disease mouse model. *PLoS One* 6, e21880

32. Huang, Z., Zhou, X., Nicholson, A. C., Gotto, A. M., Jr., Hajjar, D. P., and Han, J. (2008) Activation of peroxisome proliferator-activated receptor-alpha in mice induces expression of the hepatic low-density lipoprotein receptor. *Br J Pharmacol* 155, 596-605

33. Bahr, B. A., Abai, B., Gall, C. M., Vanderklish, P. W., Hoffman, K. B., and Lynch, G. (1994) Induction of beta-amyloid-containing polypeptides in hippocampus: evidence for a concomitant loss of synaptic proteins and interactions with an excitotoxin. *Exp Neurol* 129, 81-94

34. Nixon, R. A., and Yang, D. S. Autophagy and neuronal cell death in neurological disorders. *Cold Spring Harb Perspect Biol* 4

35. Tanida, I., Ueno, T., and Kominami, E. (2004) Human light chain 3/MAP1LC3B is cleaved at its carboxyl-terminal Met121 to expose Gly120 for lipidation and targeting to autophagosomal membranes. *J Biol Chem* 279, 47704-47710

36. Tanida, I., Ueno, T., and Kominami, E. (2004) LC3 conjugation system in mammalian autophagy. *Int J Biochem Cell Biol* 36, 2503-2518

37. Scherz-Shouval, R., and Elazar, Z. (2007) ROS, mitochondria and the regulation of autophagy. *Trends Cell Biol* 17, 422-427

38. Scherz-Shouval, R., Shvets, E., Fass, E., Shorer, H., Gil, L., and Elazar, Z. (2007) Reactive oxygen species are essential for autophagy and specifically regulate the activity of Atg4. *EMBO J* 26, 1749-1760

39. Tanida, I., Yamaji, T., Ueno, T., Ishiura, S., Kominami, E., and Hanada, K. (2008) Consideration about negative controls for LC3 and expression vectors for four colored fluorescent protein-LC3 negative controls. *Autophagy* 4, 131-134

40. Mizushima, N., and Yoshimori, T. (2007) How to interpret LC3 immunoblotting. *Autophagy* 3, 542-545

41. Tanida, I., Ueno, T., and Kominami, E. (2008) LC3 and Autophagy. *Methods Mol Biol* 445, 77-88

42. Kuma, A., Matsui, M., and Mizushima, N. (2007) LC3, an autophagosome marker, can be incorporated into protein aggregates independent of autophagy: caution in the interpretation of LC3 localization. *Autophagy* 3, 323-328

43. Zheng, L., Cedazo-Minguez, A., Hallbeck, M., Jerhammar, F., Marcusson, J., and Terman, A. Intracellular distribution of amyloid beta peptide and its relationship to the lysosomal system. *Transl Neurodegener* 1, 19

44. Orr, M. E., and Oddo, S. Autophagic/lysosomal dysfunction in Alzheimer's disease. *Alzheimers Res Ther* 5, 53

45. Parr, C., Carzaniga, R., Gentleman, S. M., Van Leuven, F., Walter, J., and Sastre, M. Glycogen synthase kinase 3 inhibition promotes lysosomal biogenesis and autophagic degradation of the amyloid-beta precursor protein. *Mol Cell Biol* 32, 4410-4418

46. Kanekiyo, T., Cirrito, J. R., Liu, C. C., Shinohara, M., Li, J., Schuler, D. R., Holtzman, D. M., and Bu, G. Neuronal clearance of amyloid-beta by endocytic receptor LRP1. *J Neurosci* 33, 19276-19283

47. Kanekiyo, T., Liu, C. C., Shinohara, M., Li, J., and Bu, G. LRP1 in brain vascular smooth muscle cells mediates local clearance of Alzheimer's amyloid-beta. *J Neurosci* 32, 16458-16465

48. Doens, D., and Fernandez, P. L. Microglia receptors and their implications in the response to amyloid beta for Alzheimer's disease pathogenesis. *J Neuroinflammation* 11, 48

49. Wyss-Coray, T., Lin, C., Yan, F., Yu, G. Q., Rohde, M., McConlogue, L., Masliah, E., and Mucke, L. (2001) TGF-beta1 promotes microglial amyloid-beta clearance and reduces plaque burden in transgenic mice. *Nat Med* 7, 612-618

50. Masliah, E., Ho, G., and Wyss-Coray, T. (2001) Functional role of TGF beta in Alzheimer's disease microvascular injury: lessons from transgenic mice. *Neurochem Int* 39, 393-400

51. Rivest, S. TREM2 enables amyloid beta clearance by microglia. *Cell Res* 25, 535-536

52. Harris, F. M., Tesseur, I., Brecht, W. J., Xu, Q., Mullendorff, K., Chang, S., Wyss-Coray, T., Mahley, R. W., and Huang, Y. (2004) Astroglial regulation of apolipoprotein E expression in neuronal cells. Implications for Alzheimer's disease. *J Biol Chem* 279, 3862-3868

53. Wyss-Coray, T., Loike, J. D., Brionne, T. C., Lu, E., Anankov, R., Yan, F., Silverstein, S. C., and Husemann, J. (2003) Adult mouse astrocytes degrade amyloid-beta in vitro and in situ. *Nat Med* 9, 453-457

54. Rolyan, H., Feike, A. C., Upadhaya, A. R., Waha, A., Van Dooren, T., Haass, C., Birkenmeier, G., Pietrzik, C. U., Van Leuven, F., and Thal, D. R. Amyloid-beta protein modulates the perivascular clearance of neuronal apolipoprotein E in mouse models of Alzheimer's disease. *J Neural Transm* (Vienna) 118, 699-712

55. Carpentier, M., Robitaille, Y., DesGroseillers, L., Boileau, G., and Marcinkiewicz, M. (2002) Declining expression of neprilysin in Alzheimer disease vasculature: possible involvement in cerebral amyloid angiopathy. *J Neuropathol Exp Neurol* 61, 849-856

56. Dorfman, V. B., Pasquini, L., Riudavets, M., Lopez-Costa, J. J., Villegas, A., Troncoso, J. C., Lopera, F., Castano, E. M., and Morelli, L. Differential cerebral deposition of IDE and NEP in sporadic and familial Alzheimer's disease. *Neurobiol Aging* 31, 1743-1757

57. Leissring, M. A., Farris, W., Chang, A. Y., Walsh, D. M., Wu, X., Sun, X., Frosch, M. P., and Selkoe, D. J. (2003) Enhanced proteolysis of beta-amyloid in APP transgenic mice prevents plaque formation, secondary pathology, and premature death. *Neuron* 40, 1087-1093

58. Farris, W., Mansourian, S., Chang, Y., Lindsley, L., Eckman, E. A., Frosch, M. P., Eckman, C. B., Tanzi, R. E., Selkoe, D. J., and Guenette, S. (2003) Insulin-degrading enzyme regulates the levels of insulin, amyloid beta-protein, and the beta-amyloid precursor protein intracellular domain in vivo. *Proc Natl Acad Sci USA* 100, 4162-4167

59. Yin, K. J., Cirrito, J. R., Yan, P., Hu, X., Xiao, Q., Pan, X., Bateman, R., Song, H., Hsu, F. F., Turk, J., Xu, J., Hsu, C. Y., Mills, J. C., Holtzman, D. M., and Lee, J. M. (2006) Matrix metalloproteinases expressed by astrocytes mediate extracellular amyloid-beta peptide catabolism. *J Neurosci* 26, 10939-10948

60. Yan, P., Hu, X., Song, H., Yin, K., Bateman, R. J., Cirrito, J. R., Xiao, Q., Hsu, F. F., Turk, J. W., Xu, J., Hsu, C. Y., Holtzman, D. M., and Lee, J. M. (2006) Matrix metalloproteinase-9 degrades amyloid-beta fibrils in vitro and compact plaques in situ. *J Biol Chem* 281, 24566-24574

61. Utter, S., Tamboli, I. Y., Walter, J., Upadhaya, A. R., Birkenmeier, G., Pietrzik, C. U., Ghebremedhin, E., and Thal, D. R. (2008) Cerebral small vessel disease-induced apolipoprotein E leakage is associated with Alzheimer disease and the accumulation of amyloid beta-protein in perivascular astrocytes. *J Neuropathol Exp Neurol* 67, 842-856

62. Thal, D. R., Larionov, S., Abramowski, D., Wiederhold, K. H., Van Dooren, T., Yamaguchi, H., Haass, C., Van Leuven, F., Staufenbiel, M., and Capetillo-Zarate, E. (2007) Occurrence and co-localization of amyloid beta-protein and apolipoprotein E in perivascular drainage channels of wild-type and APP-transgenic mice. *Neurobiol Aging* 28, 1221-1230

63. Xiao, Q., Yan, P., Ma, X., Liu, H., Perez, R., Zhu, A., Gonzales, E., Tripoli, D. L., Czerniewski, L., Ballabio, A., Cirrito, J. R., Diwan, A., and Lee, J. M. Neuronal-Targeted TFEB Accelerates Lysosomal Degradation of APP, Reducing Abeta Generation and Amyloid Plaque Pathogenesis. *J Neurosci* 35, 12137-12151

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A method for reducing amyloid-β protein aggregates in the brain of a subject, the method comprising administering to the subject in need of such treatment a composition comprising a therapeutically effective amount of a combination of vitamin A or a derivative thereof and an agonist of proliferator-activated receptor α ("PPARα").

2. The method of claim 1, therein the vitamin A derivative is retinoic acid.

3. The method of claim 1, wherein the composition further comprises at least one pharmaceutically acceptable carrier.

4. The method of claim 1, wherein the composition is administered orally.

5. The method of claim 1, wherein the composition is administered by a route selected from the group consisting of the subcutaneous, intra-articular, intradermal, intravenous, intraperitoneal and intramuscular routes.

6. The method of claim 1, wherein the composition is administered directly to the subject's central nervous system.

7. The method of claim 1, wherein the subject is exhibiting symptoms of Alzheimer's disease.

8. The method of claim 1, wherein the subject is exhibiting symptoms of Parkinsons' Disease.

9. The method of claim 1, wherein the agonist of proliferator-activated receptor α ("PPARα") is gemfibrozil.

10. A composition comprising a therapeutically effective amount of a combination of retinoic acid and an agonist of proliferator-activated receptor α ("PPARα"), wherein the therapeutically effective amount is an amount that stimulates the uptake and degradation of amyloid-ß protein by astrocytes and reduces amyloid-ß protein aggregates in the brain of a subject, and wherein the composition further comprises at least one pharmaceutically acceptable carrier.

11. The composition of claim 10, wherein the composition is administered orally.

12. The composition of claim 10, wherein the composition is administered by a route selected from the group consisting of the subcutaneous, intra-articular, intradermal, intravenous, intraperitoneal and intramuscular routes.

13. The composition of claim 10, wherein the composition is administered directly to the subject's central nervous system.

14. The composition of claim 10, wherein the subject is exhibiting symptoms of Alzheimer's disease.

15. The method of claim 10, wherein the subject is exhibiting symptoms of Parkinsons' Disease.

16. The method of claim 10, wherein the agonist of proliferator-activated receptor α ("PPARα") is gemfibrozil.

* * * * *